US008076490B2

(12) United States Patent
Reichenbach et al.

(10) Patent No.: US 8,076,490 B2
(45) Date of Patent: Dec. 13, 2011

(54) EPOTHILONES C, D, E, AND F, PREPARATION AND COMPOSITIONS (75) Inventors: Hans Reichenbach, Braunschweig (DE); Gerhard Hoefle, Braunschweig (DE); Klaus Gerth, Braunschweig (DE); Heinrich Steinmetz, Braunschweig (DE)

(73) Assignee: Helmholtz-Zentrum fuer Infektionsforschung GmbH (DE)

( * ) Notice: Subject to any disclaimer, the term of this patent is extended or adjusted under 35 U.S.C. 154(b) by 0 days.

(21) Appl. No.: 12/961,447

(22) Filed: Dec. 6, 2010

(65) Prior Publication Data
US 2011/0136185 A1 Jun. 9, 2011

Related U.S. Application Data (63) Continuation of application No. 12/409,823, filed on Mar. 24, 2009, now Pat. No. 7,846,952, which is a continuation of application No. 09/313,524, filed on May 17, 1999, now abandoned, which is a continuation of application No. PCT/EP97/06442, filed on Nov. 18, 1997.

(30) Foreign Application Priority Data

Nov. 18, 1996 (DE) .................................. 196 47 580
Feb. 25, 1997 (DE) .................................. 197 07 506

(51) Int. Cl.
    C07D 277/22 (2006.01)
(52) U.S. Cl. ...................................... 548/204
(58) Field of Classification Search .................. 548/204
    See application file for complete search history.

(56) References Cited

U.S. PATENT DOCUMENTS

| 5,057,529 A | 10/1991 | Wilson et al. |
| 5,665,767 A | 9/1997 | Fischer et al. |
| 5,969,145 A | 10/1999 | Schinzer et al. |
| 6,043,372 A | 3/2000 | Schinzer et al. |
| 6,156,905 A | 12/2000 | Schinzer et al. |
| 6,194,181 B1 | 2/2001 | Hofmann et al. |
| 6,204,388 B1 | 3/2001 | Danishefsky et al. |
| 6,211,412 B1 | 4/2001 | Georg et al. |
| 6,252,094 B1 | 6/2001 | Nicolaou et al. |
| 6,262,094 B1 | 7/2001 | Hoefle et al. |
| 6,288,237 B1 | 9/2001 | Hoefle et al. |
| 6,316,630 B1 | 11/2001 | Danishefsky et al. |
| 6,359,140 B1 | 3/2002 | Hofle et al. |
| 6,380,394 B1 | 4/2002 | Nicolaou et al. |
| 6,410,301 B1 | 6/2002 | Julien et al. |
| 6,441,186 B1 | 8/2002 | Nicolaou et al. |
| 6,489,314 B1 | 12/2002 | Ashley et al. |
| 6,531,497 B1 | 3/2003 | Nicolaou et al. |
| 6,537,988 B2 | 3/2003 | Lee |
| 6,589,968 B2 | 7/2003 | Arslanian et al. |
| 6,596,875 B2 | 7/2003 | White et al. |
| 6,605,599 B1 | 8/2003 | Vite et al. |
| 6,613,912 B2 | 9/2003 | Hoefle et al. |
| 6,624,310 B1 | 9/2003 | Hoefle et al. |
| 6,656,961 B2 | 12/2003 | Danishefsky et al. |
| 6,660,758 B1 | 12/2003 | Nicolaou et al. |
| 6,730,803 B2 | 5/2004 | Iwasaki et al. |
| 6,780,620 B1 | 8/2004 | Li et al. |
| 6,884,608 B2 | 4/2005 | Basch et al. |
| 6,906,188 B2 | 6/2005 | White et al. |
| 6,921,769 B2 | 7/2005 | Danishefsky et al. |
| 7,067,544 B2 | 6/2006 | Hoefle et al. |
| 7,235,669 B2 | 6/2007 | Hoefle et al. |
| 7,759,375 B2 | 7/2010 | Reichenbach et al. |
| 2003/0187039 A1 | 10/2003 | Favreau et al. |
| 2004/0087634 A1 | 5/2004 | Hoefle et al. |
| 2004/0127432 A1 | 7/2004 | Nicolaou et al. |
| 2004/0132146 A1 | 7/2004 | Benigni et al. |
| 2004/0176429 A1 | 9/2004 | Li et al. |
| 2008/0293784 A1 | 11/2008 | Hoefle et al. |

FOREIGN PATENT DOCUMENTS

| AU | 716610 | 3/1998 |
| CA | 1330203 | 6/1994 |
| DE | 4138042 A1 | 5/1993 |
| DE | 19542986 A1 | 5/1997 |
| DE | 19636343 C1 | 10/1997 |
| DE | 19639456 A1 | 3/1998 |
| DE | 19645361 A1 | 4/1998 |
| DE | 19645362 A1 | 4/1998 |
| DE | 19647580.5 | 5/1998 |
| DE | 19701758 A1 | 7/1998 |
| DE | 19707505 | 9/1998 |
| DE | 19713970 A1 | 10/1998 |
| DE | 19720312 A1 | 11/1998 |
| DE | 19821954 A1 | 11/1998 |
| DE | 19726627 A1 | 12/1998 |
| EP | 0 879 605 A2 | 11/1998 |
| EP | 0 903 348 | 3/1999 |
| EP | 0 941 227 | 9/1999 |
| EP | 1 186 606 | 3/2002 |
| JP | 2000-500757 | 1/2000 |
| JP | 2001-500851 | 1/2001 |

(Continued)

OTHER PUBLICATIONS

Lau, et al., "Optimizing the Heterologous Production of Epothilone D in *Myxococcus xanthus*", Biotech. & Bioengin., vol. 78, No. 3 (2002) 280-88.
Gerth, et al., "Studies on the Biosynthesis of Epothilones: The PKS and Epothilone C/D Monooxygenase", J. Antibiot., vol. 54, No. 2 (2001) 144-48.
Molnar et al., "The biosynthetic gene cluster for the microtubule-stabilizing agents epothilones A and B from *Sorangium cellulosum* So ce90", Chemistry & Biology, vol. 7, No. 2 (2000) 97-109.
Tang et al., "Cloning and Heterologous Expression of the Epothilone Gene Cluster", Science, vol. 287 (2000) 640-42.
Hardt et al., "New Natural Epothilones from *Sorangium cellullosum*, Strains So ce90/B2 and So ce90/D13: Isolation, Structure Elucidation, and SAR Studies", J. Nat. Prod., vol. 64, No. 7 (2001) 847-56.

(Continued)

*Primary Examiner* — Taofiq A Solola
(74) *Attorney, Agent, or Firm* — Finnegan, Henderson, Farabow, Garrett & Dunner, LLP (57) ABSTRACT

The present invention relates to epothilones C, D, E, and F, their preparation and their use for the production of therapeutic compositions and compositions for plant protection.

8 Claims, 5 Drawing Sheets

FOREIGN PATENT DOCUMENTS

| | | |
|---|---|---|
| WO | WO 93/10121 A1 | 5/1993 |
| WO | WO 97/19086 A1 | 5/1997 |
| WO | WO 98/08849 A1 | 3/1998 |
| WO | WO 98/22461 A1 | 5/1998 |
| WO | WO 98/24427 A2 | 6/1998 |
| WO | WO 98/25929 A1 | 6/1998 |
| WO | WO 98/38192 A1 | 9/1998 |
| WO | WO 98/47891 A1 | 10/1998 |
| WO | WO 99/01124 A1 | 1/1999 |
| WO | WO 99/02514 A2 | 1/1999 |
| WO | WO 99/03848 A1 | 1/1999 |
| WO | WO 99/07692 A2 | 2/1999 |
| WO | WO 99/39694 A2 | 8/1999 |
| WO | WO 99/42602 A2 | 8/1999 |
| WO | WO 99/43320 A1 | 9/1999 |
| WO | WO 99/43653 A1 | 9/1999 |
| WO | WO 99/67252 A2 | 12/1999 |
| WO | WO 00/00485 A1 | 6/2000 |
| WO | WO 00/31247 A1 | 6/2000 |
| WO | WO 00/37473 A1 | 6/2000 |
| WO | WO 00/49021 A2 | 8/2000 |
| WO | WO 00/66589 A1 | 11/2000 |

OTHER PUBLICATIONS

Balog, A. et al., "Total Synthesis of (−)-Epothilone A" Angew. Chem. Int. Ed. Engl., 35(23/24):2801-2803 (1996).
Bertinato, P. et al., "Studies Toward a Synthesis of Epothilone A. Stereocontrolled Assembly of the Acyl Region and Models for Macrocyclization" J. Org. Chem., 61(23):8000-8001 (1996).
Bertini, F. et al., "Alkenes from Epoxides by Reductive Elimination with Magnesium Bromide-Magnesium Amalgam" Chem. Commun., 144 (1970).
Bollag, D., "Epothilones: Novel Microtubule-Stabilising Agents" Expert Opin. Invest. Drugs, 6(7):867-873 (1997).
Bollag, D. et al., "Epothilone, A New Structural Class of Microtubule Stabilizer" Abstract, Proc. Am. Assoc. Cancer Res., 36, 86 Meet, 454 (1995).
Bollag, D.M. et al., "Epothilones, a New Structural Class of Microtubule-stabilizing Agents with a Taxol-like Mechanism of Action" Cancer Res., 55(11):2325-2333 (1995).
Chemical & Engineering News, "Epothilone Epiphany: Total Syntheses" 74(52):24-26 (1996).
Chemical & Engineering News, "First Total Synthesis of Epothilone B" 75(13):23 (1997).
Chemical & Engineering News, "Solid-Phase Epothilone Synthesis Used to Create Analog Library" 75(20)133 (1997).
Chou et al., "Desoxyepothilone B: An efficacious microtubute-targeted antitumor agent with a promising in vivo profile relative to epothilone B" Proc. Natl. Acad. Sci USA, 95:9642-9647 (1998).
Claus, E. et al., "Synthesis of the C1-C9 Segment Epothilons" Tetrahedron Lett., 38(8):1359-1362 (1997).
Corey et al., "Efficient and Mild Lactonization Method for the Synthesis of Macrolides" J. Am. Chem. Soc., 96(17):5614-5616 (1974).
De Brabander, J. et al., "Towards a Synthesis of Epothilone A: Rapid Assembly of the C1-C6 and C7-C12 Fragments" Synlett, 7:824-826 (1997).
Fujisawa, T. et al., "Deoxygenation of Epoxides to Olefins with $FeCl_3$-n-BuLI System" Chem. Lett., 883-886 (1974).
Fujiwara, Y. et al., "Reductive Coupling of Carbonyl Compounds to Olefins by Tungsten Hexachloride-Lithium Aluminum Hydride and Some Tungsten and Molybdenum Carbonyls" J. Org. Chem., 43(12):2477-2479 (1978).
Gabriel, T. and Wessjohann, L., "The Chromium-Reformatsky Reaction: Asymmetric Synthesis of the Aldol Fragment of the Cytotoxic Epothilons from 3-(2-Bromoacyl)-2-Oxazolidinones" Tetrahedron Lett., 38(8):1363-1366 (1997).
Gerth, K. et al., "Epothilons A and B: Antifungal and Cytotoxic Compounds from *Sorangiusm cellulosum* (Myxobacteria) Production, Physico-chemical and Biological Properties" J. Antibiotics, 49(6):560-563 (1996).
Gladysz, J.A. et al., "Deoxygenation of Epoxides by Metal Atom. Cocondensation" J. Org. Chem., 41(22):3647-3648 (1976).

Hofle, G. et al., "Epothilone A and B—Novel 16-Membered Macrolides Cytotoxic Activity: Isolation, Crystal Structure, and Conformation in Solution" Angew. Chem. Int. Ed. Engl. 35(13/14):1567-1569 (1996).
Hofle, G. et al., "N-Oxidation of Epothilone A-C and O-Acyl Rearrangement to C-19 and C-21—Substituted Epothilones" Angew. Chem. Int. Ed., 38(13/14):1971-1974 (1999).
Inanaga et al., "A Rapid Esterification by Means of Mixed Anhydride and Its Application to Large-ring Lactonization" Bull. Chem. Soc. Japan, 52(7):1989-1993 (1979).
Inokuchi, T. et al., "Opening of Epoxides to Olefins or Halohydrins with Vanadium(II)-Tetrahydrofuran or Vanadium(III)-Tetrahydrofuran Complexes" Synlett, 6:510-512 (1992).
International Search Report issued in International Patent Application No. PCT/EP97/06442; Date of Mailing: Apr. 9, 1998.
International Preliminary Examination Report issued in International Patent Application No. PCT/EP97/01442; Date of Mailing: Feb. 11, 1999.
Kowalski, R.J. et al., "Activities of the Microtubule-stabilizing Agents Epothilones A and B with Purified Tubulin and in Cells Resistant to Paclitaxel (Taxol.RTM.)" J. Biol. Chem., 272(4):2534-2541 (1997).
Kruizinga et al., "Preparation of Macrocyclic Lactones by Ring Closure of Cesium Carboxylates" J. Am. Chem. Soc., 103(17):5183-5189 (1981).
Kupchan, S.M. et al., "Reductive Elimination of Epoxides to Olefins with Zinc-Copper Couple" J. Org. Chem., 36(9):1187-1190 (1971).
Marshall, A., "Total Synthesis of Epothilone" Nature Biotechnology, 15(3):205 (1997).
Martin, M.G. et al., "Epoxides as Alkene Protectino Groups. A Mild and Efficient Deoxygenation" Tetrahedron Letters, 25(3):251-254 (1984).
McMurry, J.E. et al., "Reduction of Epoxides to Olefins with Low Valent Titanium" J. Org Chem., 40(17):2555-2556 (1975).
McMurry, J.E. et al., "Some Deoxygenation Reactions with Low-Valent Titanium ($TiCl_3/LiAlH_4$)" J. Org. Chem. 43(17):3249-3254 (1978).
Meng, D. et al. "Remote Effects in Macrolide Formation Through Ring-Forming Olefin Metathesis: An Application to the Synthesis of Fully Active Epothilone Congeners" J. Am. Chem. Soc., 119(11):2733-2734 (1997).
Meng, D. et al., "Studies Toward a Synthesis of Epothilone A: Use of Hydropyran Templates for the Management of Acyclic Stereochemical Relationships" J. Org. Chem., 61(23):7998-7999 (1996).
Meng, D. et al., "Total Syntheses of Epothilones A and B" J. Am. Chem. Soc., 119(42):10073-10092 (1997).
Mensching, S. and Kalesse, M., "Generation of Thiazoles by Column Dehydrogenation of Thiazolidines with $MnO_2$" J. Prakt. Chem., 339(1):96-97 (1997).
Mulzer, J. and Mantoulidis, A., "Synthesis of the C(1)-C(9) Segment of the Cytotoxic Macrolides Epothilon A and B" Tetrahedron Lett., 37(51):9179-9182 (1996).
Nicolaou et al., "Chemical Biology of Epothilones" Angew. Chem. Int. Ed., 37:2014-2045 (1988).
Nicolaou et al., "Total Synthesis of Epothilone E and Analogs with Modified Side Chains Through The Stille Coupling Reaction" Angew. Chem. Int. Ed., 37:84-87 (1998).
Nicolaou et al., "Total Synthesis of Oxazole- and Cyclopropane-Containing Epothilone B Analogues by the Macrolactonization Approach" Chemistry, European Journal, 3(12):1971-1986 (1997).
Nicolaou, K.C. et al., "An Approach to Epothilones Based on Olefin Metathesis" Angew. Chem. Int. Ed. Engl., 35(20):2399-2401 (1996).
Nicolaou, K.C. et al., "Synthesis and Biological Properties of C12,13-Cyclopropylepothilone A and Related Epothilones" Chemistry & Biology, 5(7):365-372 (1998).
Nicolaou, K.C. et al., "Synthesis of Epothilones A and B in Solid and Solution Phase" Nature, 387:268-272 (1997).
Nicolaou, K.C. et al., "Synthesis of Epothilones A and B in Solid and Solution Phase" (Correction to Nature 387, 268-272 (1997)) Nature, 390:100 (1997).
Nicolaou, K.C. et al., "Total Syntheses of Epothilones A and B via a Macrolactonization-Based Strategy" J. Am. Chem. Soc., 119(34):7974-7991 (1997).

Nicolaou, K.C. et al., "Total Synthesis of Epothilone A: The Macrolactonization Approach" Angew. Chem. Int. Ed. Engl., 36, No. 5, 525-527 (1997).

Nicolaou, K.C. et. al., "Designed Epothilones: Combinatorial Synthesis, Tubulin Assembly Properties, and Cytotoxic Action against Taxol-Resistant Tumor Cells" Angew Chem. Int. Ed. Engl., 36(19):2097-2103 (1997).

Nicolaou, K. et al., "Chemistry, Biology and Medicine of Selected Tubulin Polymerizing Agents" Pure Appl. Chem., 71(6):989-997 (1999).

Nicolaou, K., et al., "Total Synthesis of Epothilone E and Related Side-chain Modified Analogues via a Stille Coupling Based Strategy" Biorg. Med. Chem., 7(5):665-697 (1999).

Nicolaou, K.C. et al., "The Olefin Metathesis Approach to Epothilone A and its Analogues" J. Am. Chem. Soc., 119(34):7960-7973 (1997).

Raucher, S. et al., "Total Synthesis of (+)-Dihydrocostunolide via Tandem Cope-Claisen Rearrangement" J. Org. Chem., 51(26):5503-5505 (1986).

Sato, M. et al., "Reduction of Organic Compounds with Low-Valent Niobium (NbCl$_5$/NaAlH$_4$)" Chem. Letters, 157-160 (1982).

Schinzer, D. et al., "Studies Towards the Total Synthesis of Epothilones: Asymmetric Synthesis of the Key Fragments" Chem. Eur. J., 2(22):1477-1482 (1996).

Schinzer, D. et al., "Syntheses of (−)-Epothilone A" Chem. Eur. J., 5(9):2483-2491 (1999).

Schinzer, D. et al., "Syntheses of (-31)-Epothilone B" Chem. Eur. J., 5(9)2492-2500 (1999).

Schinzer, D. et al., "Total Synthesis of (−)-Epothilone A" Angew. Chem. Int. Ed. Engl., 36(5):523-524 (1997).

Schobert, R. et al., "Reduction and Isomerization of Oxiranes and alpha.-Diazoketones by Various Early Transition Metallocenes" Synlett, 8:465-466 (1990).

Sharpless, K. B. et al., "Lower Valent Tungsten Halides. A New Class of Reagents for Deoxygenation of Organic Molecules" J. Amer. Chem. Soc., 94(18):6538-6540 (1972).

Su, D.-S. et al., "Structure-Activity Relationships of the Epothilones and First In Vivo Comparison with Paclitaxel" Angew. Chem. Int. Ed. Engl., 36(19):2093-2096 (1997).

Su, D.-S. et al., "Total Synthesis of (−)-Epothilone B: An Extension of the Suzuki Coupling Method and Insights into Structure-Activity Relationships of the Epothilones" Angew. Chem. Int. Ed. Engl., 36(7):757-759 (1997).

Taylor, R. and Haley, J., "Towards the Synthesis of Epothilone A: Enantioselective Preparation of the Thiazole Sidechain and Macrocyclic Ring Closure" Tetrahedron Lett., 38(12):2061-2064(1997).

U.S. Appl. No. 60/032,864, filed Dec. 13, 1996, Nicolaou, K., et al.

U.S. Appl. No. 08/856,533, Nicolaou et al., filed May 14, 1997, now abandoned.

Victory, S.F. et al., "Relative Stereochemistry and Solution Conformation of the Novel Paclitaxel-Like Antimitotic Agent Epothilone A" Bioorg. Med. Chem. Letts., 6(7):893-898 (1996).

Winkler, J.D. et al., "A Model for the Taxol (Paclitaxel)/Epothilone Pharmacophore" Bioorg. Med. Chem. Letts., 6(24):2963-2966 (1996).

Yang, Z. et al., "Total Synthesis of Epothilone A: The Olefin Metathesis Approach" Angew. Chem. Int. Ed. Engl., 36(1/2):166-168 (1997).

EPOTHILONES C, D, E, AND F, PREPARATION AND COMPOSITIONS

This application is a continuation of U.S. application Ser. No. 12/409,823, filed on Mar. 24, 2009, and issued as U.S. Pat. No. 7,846,952 on Dec. 7, 2010, which is a continuation of U.S. application Ser. No. 09/313,524, filed on May 17, 1999, now abandoned, which is a continuation of PCT Application No. PCT/EP97/06442, filed on Nov. 18, 1997, which claims priority to German Application Nos. DE 197 07 506.1, filed on Feb. 25, 1997, and DE 196 47 580.5, filed on Nov. 18, 1996. The disclosure of each of the above applications is incorporated by reference in its entirety.

The present invention relates to epothilones C, D, E and F, their preparation and their use for the production of therapeutic compositions and compositions for plant protection.

Epothilones C and D

According to one embodiment, the invention relates to epothilones [C and D] which are obtainable in that (a) *Sorangium cellulosum* DSM 6773 is cultured in a manner known per se in the presence of an adsorber resin, (b) the adsorber resin is removed from the culture and washed with a water/methanol mixture, (c) the washed adsorber resin is eluted with methanol and the eluate is concentrated to give a crude extract, (d) the concentrate obtained is extracted with ethyl acetate, the extract is concentrated and partitioned between methanol and hexane, (e) the methanolic phase is concentrated to give a raffinate and the concentrate is fractionated on a Sephadex column, (f) a fraction containing metabolic products of the microorganism employed is obtained, (g) the fraction obtained is chromatographed on a C18 reverse phase to a methanol/water mixture and, sequentially after a first fraction containing epothilone A and a second fraction containing epothilone B a third fraction containing a first further epothilone and a fourth fraction containing a second further epothilone are obtained and (h1) the epothilone of the first further fraction and/or (h2) the epothilone of the second further fraction are isolated.

The invention further relates to an epothilone [C] of the empirical formula $C_{26}H_{39}NO_5S$, characterized by the $^1H$- and $^{13}C$-NMR spectrum as in Table 1.

The invention furthermore relates to epothilone C of the formula:

Epothilone C R=H.

The invention furthermore relates to epothilone [D] of the empirical formula $C_{27}H_{41}NO_5S$, characterized by the $^1H$- and $^{13}C$-NMR spectrum as in Table 1.

The invention furthermore relates to epothilone D of the formula:

Epothilone D R=CH$_3$.

Epothilones C and D can be used for the preparation of the compounds of the following formula 1, where for their derivatization reference can be made to the derivatization methods described in WO-A-97/19 086.

In the above formula 1:
R=H,
$R^1$, $R^2$, $R^3$, $R^4$, $R^5$=H, $C_{1-6}$-alkyl,
$C_{1-6}$-acylbenzoyl,
$C_{1-4}$-trialkylsilyl,
benzyl,
phenyl,
$C_{1-6}$-alkoxy-,
$C_6$-alky-, hydroxy- and halogen-substituted benzyl or phenyl;
where two of the radicals $R^1$ to $R^5$ can also combine to form the group —$(CH_2)_n$— with n=1 to 6 and the alkyl or acyl groups contained in the radicals are straight-chain or branched radicals; Y and Z are either identical or different and are each hydrogen, halogen, such as F, Cl, Br or I, pseudohalogen, such as —NCO, —NCS or —N$_3$, OH, O—($C_{1-6}$)-acyl, O—($C_{1-6}$)-alkyl, O-benzoyl. Y and Z can also be the O atom of an epoxide, epothilone A and B not being claimed, or form one of the C—C bonds of a C=C double bond.

Thus the 12, 13-double bond can be selectively
  hydrogenated, for example catalytically or with diimine, a compound of the formula 1 being obtained with Y=Z=H; or
  epoxidized, for example with dimethyldioxirane or a peracid, a compound of the formula 1 being obtained with Y and Z=—O—; or
  converted into the dihalides, dipseudohalides or diazides, a compound of the formula 1 being obtained with Y and Z=Hal, pseudo-hal or N$_3$.

Epothilones E and F

According to a further embodiment the invention relates to a biotransformant of epothilone A, which is obtainable in that (a) *Sorangium cellulosum* DSM 6773 is cultured in a manner known per se in the presence of an adsorber resin, removed from the adsorber resin and, if appropriate, the total amount or a part of the separated culture is treated with a methanolic solution of epothilone A, (b) the culture treated with epothilone A is incubated and then treated with adsorber resin, (c) the adsorber resin is separated from the culture, eluted with methanol and the eluate is concentrated to give a crude extract, (d) the crude extract is partitioned between ethyl acetate and water, the ethyl acetate phase is separated off and concentrated to give an oil, (e) the oil is chromatographed on a reverse phase under the following conditions:

| | |
|---|---|
| column material: | Nucleosil 100 C-18 7 μm |
| column dimensions: | 250 × 16 mm |
| eluent: | methanol/water = 60:40 |
| flow rate: | 10 ml/min | and fractions having a content of biotransformant and which can be detected by UV extinction at 254 nm and have an $R_t$ value of 20 min are separated off and the biotransformants are isolated.

The invention furthermore relates to a biotransformant of epothilone A of this type, which is obtainable in that in stage (a) a culture is separated off which is three or four or more days old.

The invention furthermore relates to a biotransformant of epothilone A of this type, which is obtainable in that in stage (b) incubation is carried out for one or two or more days.

The invention furthermore relates to a compound of the empirical formula $C_{26}H_{39}NO_7S$, characterized by the following $^1$H-NMR spectrum (300 MHz, CDCl$_3$): delta=2.38 (2-H$_a$), 2.51 (2-H$_b$), 4.17 (3-H), 3.19 (6-H), 3.74 (7-H), 1.30-1.70 (8-H, 9-H$_2$, 10-H$_2$, 11-H$_2$), 2.89 (12-H), 3.00 (13-H), 1.88 (14-H$_a$), 2.07 (14-H$_b$), 5.40 (15-H), 6.57 (17-H), 7.08 (19-H), 4.85 (21-H$_2$), 1.05 (22-H$_3$), 1.32 (23-H$_3$), 1.17 (24-H$_3$), 0.97 (25-H$_3$), 2.04 (27-H$_3$).

The invention furthermore relates to a compound (epothilone E) of the formula:

Epothilone E R=H

According to a further embodiment, the invention relates to a biotransformant of epothilone B, which is obtainable in that (a) *Sorangium cellulosum* DSM 6773 is cultured in a manner known per se in the presence of an adsorber resin, separated from the adsorber resin and, if appropriate, the total amount or a part of the separated culture is treated with a methanolic solution of epothilone B, (b) the culture treated with epothilone B is incubated and then treated with adsorber resin, (c) the adsorber resin is separated from the culture, eluted with methanol and the eluate is concentrated to give a crude extract, (d) the crude extract is partitioned between ethyl acetate and water, the ethyl acetate phase is separated off and concentrated to give an oil, (e) the oil is chromatographed on a reverse phase under the following conditions:

| | |
|---|---|
| column material: | Nucleosil 100 C-18 7 μm |
| column dimensions: | 250 × 16 mm |
| eluent: | methanol/water = 60:40 |
| flow rate: | 10 ml/min | and fractions having a content of biotransformant and which can be detected by UV extinction at 254 nm and have an $R_t$ value of 24.5 min are separated off and the biotransformants are isolated.

The invention furthermore relates to a biotransformant of epothilone B of this type, which is obtainable in that in stage (a) a culture is separated off which is three or four or more days old.

The invention furthermore relates to a biotransformant of epothilone B of this type, which is obtainable in that in stage (b) incubation is carried out for one or two or more days.

The invention furthermore relates to a compound of the empirical formula $C_{27}H_{41}NO_7S$, characterized by the following $^1$H-NMR spectrum (300 MHz, CDCl$_3$): delta=2.37 (2-H$_a$), 2.52 (2-H$_b$), 4.20 (3-H), 3.27 (6-H), 3.74 (7-H), 1.30-1.70 (8-H, 9-H$_2$, 10-H$_2$, 11-H$_2$), 2.78 (13-H), 1.91 (14-H), 2.06 (14-H$_b$), 5.42 (15-H), 6.58 (17-H), 7.10 (19-H), 4.89 (21-H$_2$), 1.05 (22-H$_3$), 1.26 (23-H$_3$), 1.14 (24-H$_3$), 0.98 (25-H$_3$), 1.35 (26-H$_3$), 2.06 (27-H$_3$).

The invention furthermore relates to a compound (epothilone F) of the formula:

Epothilone F R=CH$_3$

PREPARATION AND COMPOSITIONS

The compounds or epothilones according to the invention are obtainable by the abovementioned measures.

The invention furthermore relates to compositions for plant protection in agriculture, forestry and/or horticulture, consisting of one or more of the abovementioned epothilones C, D, E and F or consisting of one or more of the abovementioned epothilones in addition to one or more customary carrier(s) and/or diluent(s).

The invention finally relates to therapeutic compositions, consisting of one or more of the abovementioned compounds or one or more of the abovementioned compounds in addition to one or more customary carrier(s) and/or diluent(s). In particular, these compositions can show cytotoxic activities and/or bring about immunosuppression and/or be employed for the control of malignant tumours, it being particularly preferably possible for them to be used as cytostatics.

In the following, the invention is illustrated and described in greater detail by the description of some selected working examples.

EXAMPLES

Example 1

Epothilones C and D

A. Production Strain and Culture Conditions According to the Epothilone Basic Patent DE-B-41 38 042.

B. Production with DSM 6773

75 l of culture are grown as described in the basic patent and used for the inoculation of a production fermenter with 700 l of production medium consisting of 0.8% starch, 0.2% glucose, 0.2% soya flour, 0.2% yeast extract, 0.1% $CaCl_2 \times 2H_2O$, 0.1% $MgSO_4 \times 7H_2O$, 8 mg/l of Fe-EDTA, pH=7.4 and optionally 15 l of Amberlite XAD-16 adsorber resin. The fermentation lasts 7-10 days at 30 C, aeration with 2 m³/hr. By controlling the speed of rotation, the $pO_2$ is kept at 30%.

C. Isolation

The adsorber resin is separated from the culture using a 0.7 m², 100 mesh process filter and freed from polar concomitants by washing with 3 bed volumes of water/methanol 2:1. By elution with 4 bed volumes of methanol, a crude extract is obtained which is evaporated in vacuo until the water phase appears. This is extracted three times with the same volume of ethyl acetate. Evaporation of the organic phase affords 240 g of crude extract, which is partitioned between methanol and heptane in order to separate off lipophilic concomitants. By evaporation in vacuo, 180 g of raffinate are obtained from the methanol phase and are fractionated into three portions on Sephadex LH-20 (column 20×100 cm, 20 ml/min of methanol). The epothilones are contained in the fraction of a total of 72 g eluted with a 240-300 min retention time. To separate the epothilones, the fraction is chromatographed in three portions on Lichrosorb RP-18 (15 μm, column 10×40 cm, eluent 180 ml/min methanol/water 65:35). After epothilone A and B, epothilone C, with $R_t$=90-95 min, and epothilone D, 100-110 min, are eluted and after evaporation in vacuo obtained in a yield of 0.3 g each as colourless oils.

D. Physical Properties

Epothilone C R=H
Epothilone D R=CH3
Epothilone C
$C_{26}H_{39}NO_5S$ [477]
ESI-MS: (positive ions): 478.5 for $[M+H]^+$
1H and 13C see NMR table
TLC: $R_f$=0.82
TLC aluminum foil 60 F 254 Merck, eluent: dichloromethane/methanol=9:1
Detection: UV extinction at 254 nm. Spraying with vanillin-sulphuric acid reagent, blue-grey coloration on heating to 120° C.
HPLC: $R_t$=11.5 min
Column: Nucleosil 100 C-18 7 μm, 125×4 mm
Eluent: methanol/water=65:35
Flow rate: 1 ml/min
Detection: diode array
Epothilone D
$C_{27}H_{41}NO_5S$ [491]
ESI-MS: (positive ions): 492.5 for $[M+H]^+$
1H and 13C see NMR table
TLC: $R_f$=0.82
TLC aluminum foil 60 F 254 Merck, eluent: dichloromethane/methanol=9:1
Detection: UV extinction at 254 nm. Spraying with vanillin-sulphuric acid reagent, blue-grey coloration on heating to 120° C.
HPLC: $R_t$=15.3 min
Column: Nucleosil 100 C-18 7 μm, 125×4 mm
Eluent: methanol/water=65:35
Flow rate: 1 ml/min
Detection: diode array

TABLE 1

¹H- and ¹³C-NMR data of epothilone C and epothilone D in [D₆] DMSO at 300 MHz

| | Epothilone C | | | Epothilone D | | |
|---|---|---|---|---|---|---|
| H atom | δ (ppm) | C atom | δ (ppm) | δ (ppm) | C atom | δ (ppm) |
| | | 1 | 170.3 | | 1 | 170.1 |
| 2-Ha | 2.38 | 2 | 38.4 | 2.35 | 2 | 39.0 |
| 2-Hb | 2.50 | 3 | 71.2 | 2.38 | 3 | 70.8 |
| 3-H | 3.97 | 4 | 53.1 | 4.10 | 4 | 53.2 |
| 3-OH | 5.12 | 5 | 217.1 | 5.08 | 5 | 217.4 |
| 6-H | 3.07 | 6 | 45.4 | 3.11 | 6 | 44.4 |
| 7-H | 3.49 | 7 | 75.9 | 3.48 | 7 | 75.5 |
| 7-OH | 4.46 | 8 | 35.4 | 4.46 | 8 | 36.3 |
| 8-H | 1.34 | 9 | 27.6 | 1.29 | 9 | 29.9 |
| 9-Ha | 1.15 | 10 | 30.0 | 1.14 | 10 | 25.9 |
| 9-Hb | 1.40 | 11 | 27.6 | 1.38 | 11 | 31.8* |
| 10-Ha | 1.15* | 12 | 124.6 | 1.14* | 12 | 138.3 |
| 10-Hb | 1.35* | 13 | 133.1 | 1.35* | 13 | 120.3 |
| 11-Ha | 1.90 | 14 | 31.1 | 1.75 | 14 | 31.6* |
| 11-Hb | 2.18 | 15 | 76.3 | 2.10 | 15 | 76.6 |
| 12-H | 5.38** | 16 | 137.3 | | 16 | 137.2 |

TABLE 1-continued

¹H- and ¹³C-NMR data of epothilone C and epothilone D in [D₆] DMSO at 300 MHz

| H atom | Epothilone C δ (ppm) | C atom | δ (ppm) | Epothilone D δ (ppm) | C atom | δ (ppm) |
|---|---|---|---|---|---|---|
| 13-H | 5.44** | 17 | 119.1 | 5.08 | 17 | 119.2 |
| 14-Ha | 2.35 | 18 | 152.1 | 2.30 | 18 | 152.1 |
| 14-Hb | 2.70 | 19 | 117.7 | 2.65 | 19 | 117.7 |
| 15-H | 5.27 | 20 | 164.2 | 5.29 | 20 | 164.3 |
| 17-H | 6.50 | 21 | 18.8 | 6.51 | 21 | 18.9 |
| 19-H | 7.35 | 22 | 20.8 | 7.35 | 22 | 19.7 |
| 21-H₃ | 2.65 | 23 | 22.6 | 2.65 | 23 | 22.5 |
| 22-H₃ | 0.94 | 24 | 16.7 | 0.90 | 24 | 16.4 |
| 23-H₃ | 1.21 | 25 | 18.4 | 1.19 | 25 | 18.4 |
| 24-H₃ | 1.06 | 27 | 14.2 | 1.07 | 26 | 22.9 |
| 25-H₃ | 0.90 | | | 0.91 | 27 | 14.1 |
| 26-H₃ | | | | 1.63 | | |
| 27-H₃ | 2.10 | | | 2.11 | | |

*,**assignment interchangeable

Example 2

Epothilone A and 12,13-bisepi-epothilone A from Epothilone C 50 mg of epothilone A are dissolved in 1.5 ml of acetone and treated with 1.5 ml of a 0.07 molar solution of dimethyldioxirane in acetone. After standing at room temperature for 6 hours, the mixture is evaporated in vacuo and the residue is separated by preparative HPLC on silica gel (eluent: methyl tert-butyl ether/petroleum ether/methanol 33:66:1).

Yield:
25 mg of epothilone A, $R_f$=3.5 min (analyt. HPLC, 7 µm, column 4×250 mm, eluent see above, flow rate 1.5 ml/min)
and
20 mg of 12,13-bisepi-epothilone A, $R_f$=3.7 min, ESI-MS (pos. ions) m/e=494
$[M+H]^+$
¹H-NMR in [D₄] methanol, selected signals: delta=4.32 (3-H), 3.79 (7-H), 3.06 (12-H), 3.16 (13-H), 5.54 (15-H), 6.69 (17-H), 1.20 (22-H), 1.45 (23-H).

12,13-bisepi-epothilone A R=H

Example 3

Epothilone E and F, Novel Biotransformation Products of Epothilones A and B

Production Strain:
The production strain *Sorangium cellulosum* So ce90 was isolated in July 1985 in GBF from a soil sample from the banks of the Zambesi and deposited on 28.10.91 in the German Collection for Microorganisms under No. DSM 6773.

The characterization of the producer and the culture conditions are described in:

Höfle, G.; N. Bedorf, K. Gerth & H. Reichenbach: Epothilones, processes for their preparation and compositions containing them. DE 41 38 042 A1, laid open on 27 May 1993.

Formation of Epothilones E and F During Fermentation:

A typical fermentation proceeds in the following manner: A 100 l bioreactor is filled with 60 l of medium (0.8% starch; 0.2% glucose; 0.2% soya flour; 0.2% yeast extract; 0.1% $CaCl_2×2H_2O$; 0.1% $MgSO_4×7H_2O$; 8 mg/l of Fe-EDTA; pH 7.4). 2% of adsorber resin (XAD-16, Rohm & Haas) are additionally added. The medium is sterilized by autoclaving (2 hours, 120° C.). Inoculation is carried out with 10 l of a preculture grown in the same medium (additionally 50 mM HEPES buffer pH 7.4) in a shaker flask (160 rpm, 30° C.). Fermentation is carried out at 32° C. with a stirrer speed of 500 rpm and an introduction of 0.2 N1 per m³ per hour of air, the pH is kept at 7.4 by addition of KOH. The fermentation lasts 7 to 10 days. The epothilones formed are continuously bound to the adsorber resin during the fermentation. After separating off the culture broth (e.g. by screening in a process filter), the resin is washed with 3 bed volumes of water and eluted with 4 bed volumes of methanol. The eluate is concentrated to dryness and taken up in 700 ml of methanol.

HPLC Analysis of the XAD Eluate:

In relation to the starting volume of the reactor (70 l), the eluate is concentrated 100:1. The analysis is carried out using a 1090 HPLC unit from Hewlett Packard. To separate the constituents, a microbore column (125/2 Nucleosil 120-5 $C_{18}$) from Machery-Nagel (Düren) is used. Elution is carried out using a gradient of water/acetonitrile from initially 75:25 up to 50:50 after 5.5 minutes. This ratio is maintained up to the 7th minute, in order to then increase it up to the 10th minute to 100% acetonitrile.

Figure 1:
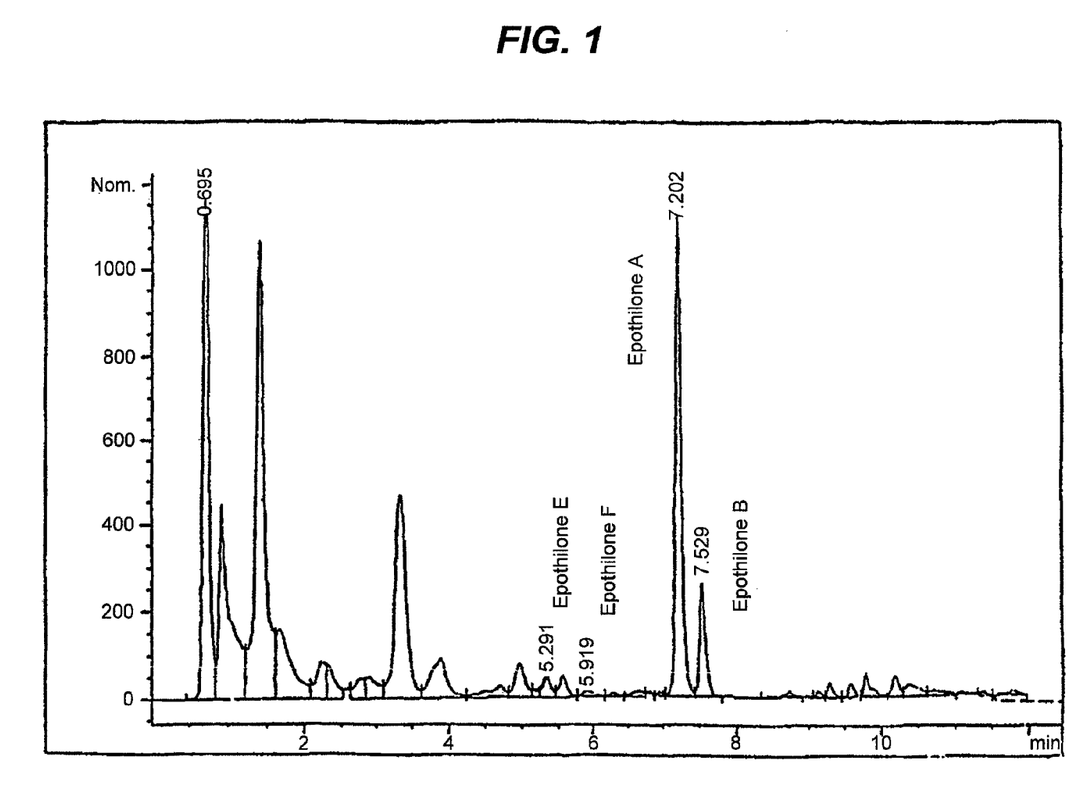
FIG. 1 shows a HPLC analysis of an XAD eluate at the end of a fermentation.

Measurement is carried out at a wavelength of 250 nm and a bandwidth of 4 nm. The diode array spectra are measured in the wavelength range from 200 to 400 nm. In the XAD eluate, two novel substances with $R_t$ 5.29 and $R_t$ 5.91 stand out, whose adsorption spectra are identical with those of epothilones A and B (FIG. 1; E corresponds to A, F corresponds to B). These substances are only formed in traces under the given fermentation conditions.

Figure 2:
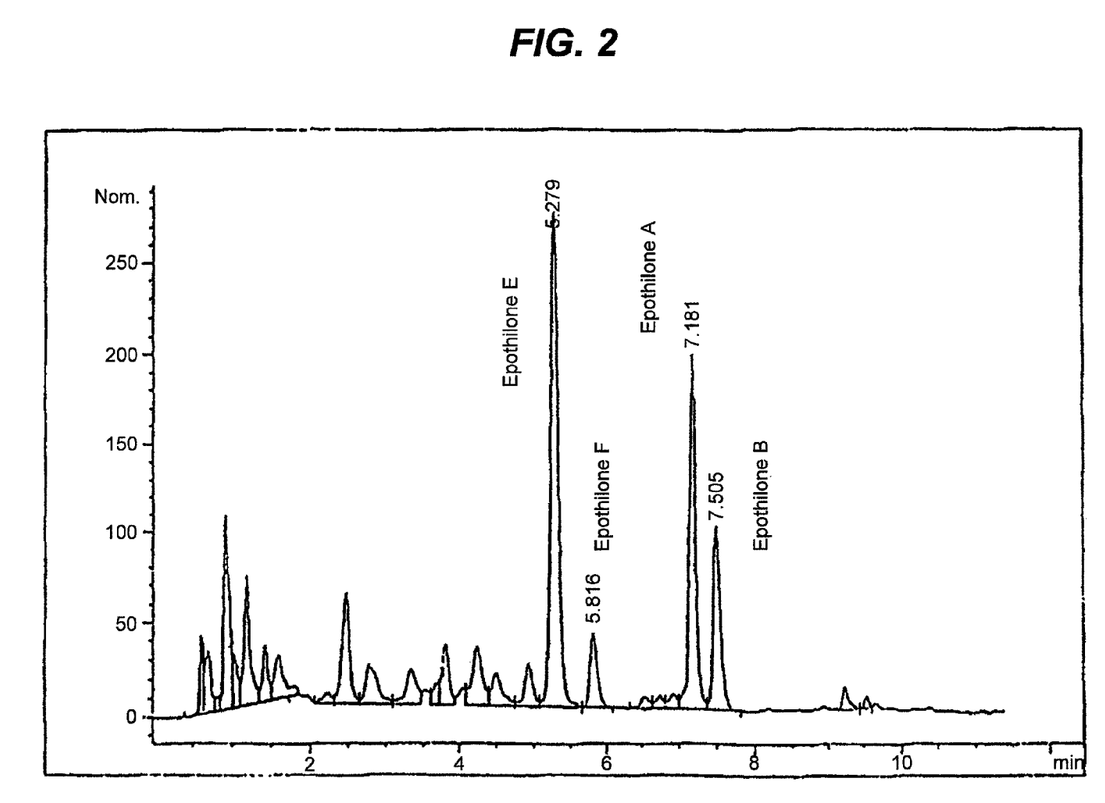
FIG. 2 shows an enrichment of epothilone E and F in a fermentation broth after feeding of a mixture of epothilone A and B, analysed after incubation for 48 hours.
Figure 3:
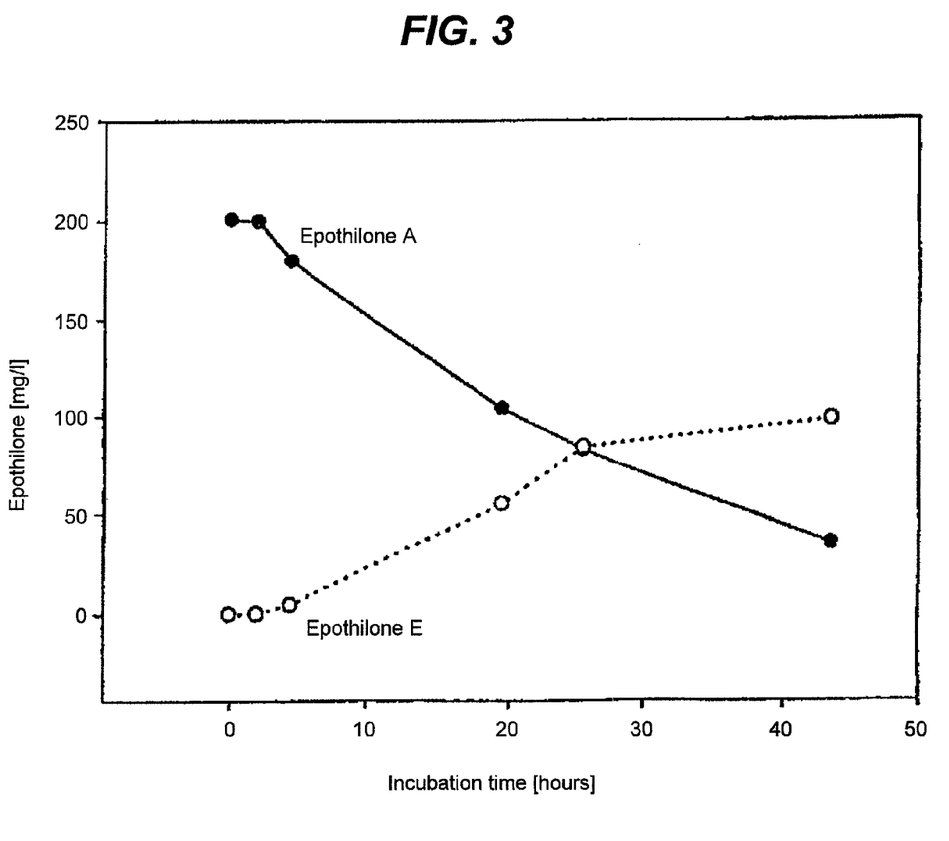
FIG. 3 shows kinetics of the biotransformation of epothilone A to epothilone E by *Sorangium cellulosum* So ce90.

Biotransformation of Epothilone A and B to Epothilone E and F:

A 500 ml culture of So ce90, 4 days old and maintained with adsorber resin, is used for the specific biotransformation. 250 ml of this are transferred to a sterile 1 l Erlenmeyer flask leaving behind the XAD. A methanolic solution of a mixture of a total of 36 mg of epothilone A+14 mg of B is then added and the flask is incubated on a shaking rack for two days at 30° C. and 200 rpm. The formation of the epothilones E and F is analysed directly from 10 µl of the centrifuged culture supernatant (FIG. 2). The conversion takes place only in the presence of the cells and is dependent on the cell densities employed and the time. Kinetics of the conversion are shown for epothilone A in FIG. 3.

Isolation of Epothilone E and F

To isolate epothilone E and F, three shaker flask batches from the biotransformation (see above) are combined and shaken with 20 ml of XAD-16 for 1 h. The XAD is obtained by screening and eluted with 200 ml of methanol. The eluate is evaporated in vacuo to give 1.7 g of crude extract. This is partitioned between 30 ml of ethyl acetate and 100 ml of water. On evaporation in vacuo, 330 mg of an oily residue are obtained from the ethyl acetate phase, which are chromatographed in five runs on a 250×20 mm RP-18 column (eluent: methanol/water 58:42, detection 254 nm).

Yield: epothilone E 50 mg
F 10 mg

Biological Action of Epothilone E:

In cell cultures, the concentration was determined which reduces the growth by 50% ($IC_{50}$) and compared with the values for epothilone A.

| Cell line | IC50 (ng/ml) | |
|---|---|---|
| | Epothilone E | Epothilone A |
| HeLa.KB-3.1 (human) | 5 | 1 |
| Mouse fibroblasts, L929 | 20 | 4 |

Epothilone E
$C_{26}H_{30}HO_7S$ [509]
ESI-MS: (positive ions): 510.3 for $[M+H]^+$
TLC: $R_f$=0.58
TLC aluminum foil 60 F 254 Merck, eluent: dichloromethane/methanol=9:1
Detection: UV extinction at 254 nm. Spraying with vanillin-sulphuric acid reagent, blue-grey colouration on heating to 120° C.
HPLC: $R_f$=5.0 min
Column: Nucleosil 100 C-18 7 µm, 250×4 mm
Eluent: methanol/water=60:40
Flow rate: 1.2 ml/min
Detection: diode array
$^1$H-NMR (300 MHz, $CDCl_3$): delta=2.38 (2-$H_a$), 2.51 (2-$H_b$), 4.17 (3-H), 3.19 (6-H), 3.74 (7-H), 1.30-1.70 (8-H, 9-$H_2$, 10-$H_2$, 11-$H_2$), 2.89 (12-H), 3.00 (13-H), 1.88 (14-$H_a$), 2.07 (14-$H_b$), 5.40 (15-H), 6.57 (17-H), 7.08 (19-H), 4.85 (21-$H_2$), 1.05 (22-$H_3$), 1.32 (23-$H_3$), 1.17 (24-$H_3$), 0.97 (25-$H_3$), 2.04 (27-$H_3$)

Epothilone F
$C_{27}H_{41}NO_7S$ [523]
ESI-MS: (positive ions): 524.5 for $[M+H]^+$
TLC: $R_f$=0.58
TLC aluminum foil 60 F 254 Merck, eluent: dichloromethane/methanol=9:1
Detection: UV extinction at 254 nm. Spraying with vanillin-sulphuric acid reagent, blue-grey colouration on heating to 120° C.
HPLC: $R_f$=5.4 min
Column: Nucleosil 100 C-18 7 µm, 250×4 mm
Eluent: methanol/water=60:40
Flow rate: 1.2 ml/min
Detection: diode array
$^1$H-NMR (300 MHz, $CDCl_3$): delta=2.37 (2-$H_a$), 2.52 (2-$H_b$), 4.20 (3-H), 3.27 (6-H), 3.74 (7-H), 1.30-1.70 (8-H, 9-$H_2$, 10-$H_2$, 11-$H_2$), 2.78 (13-H), 1.91 (14-H), 2.06 (14-$H_b$), 5.42 (15-H), 6.58 (17-H), 7.10 (19-H), 4.89 (21-$H_2$), 1.05 (22-$H_3$), 1.26 (23-$H_3$), 1.14 (24-$H_3$), 0.98 (25-$H_3$), 1.35 (26-$H_3$), 2.06 (27-$H_3$).

Example 4

Preparation of Epothilone E and F by Biotransformation with *Sorangium cellulosum* So ce90

Figure 4:
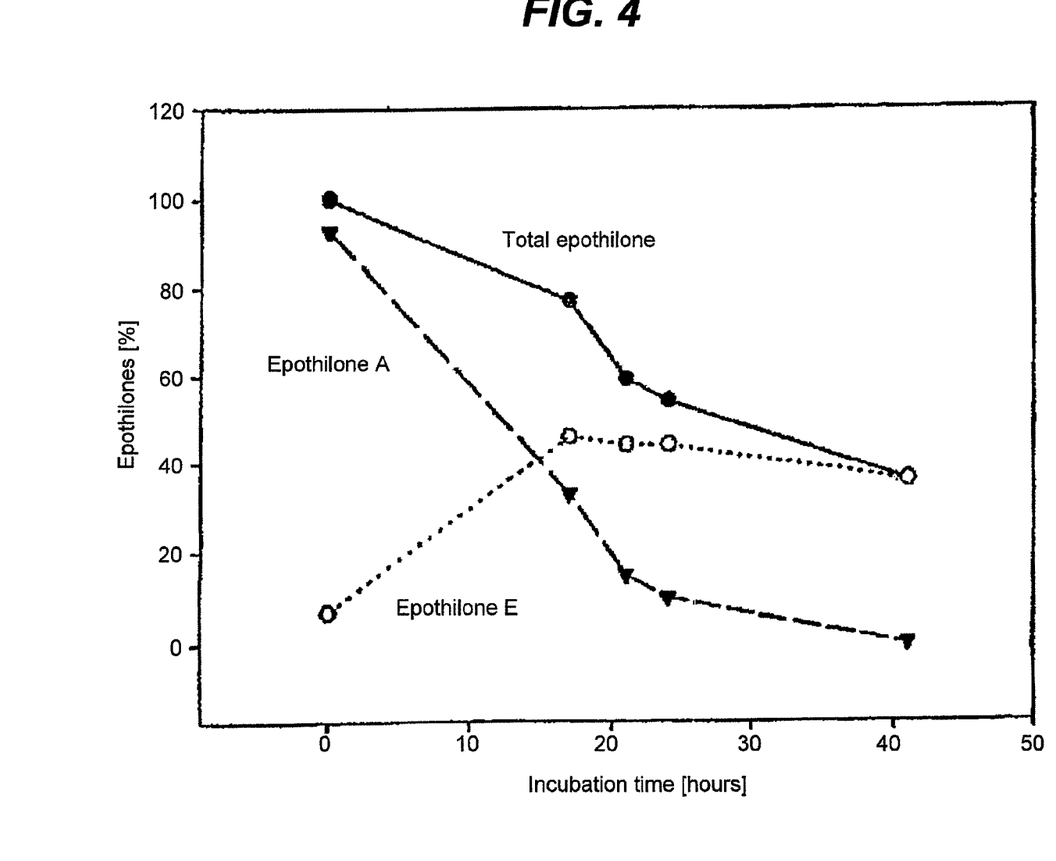
FIG. 4 shows biotransformation of epothilone. A to epothilone E.
Figure 5:
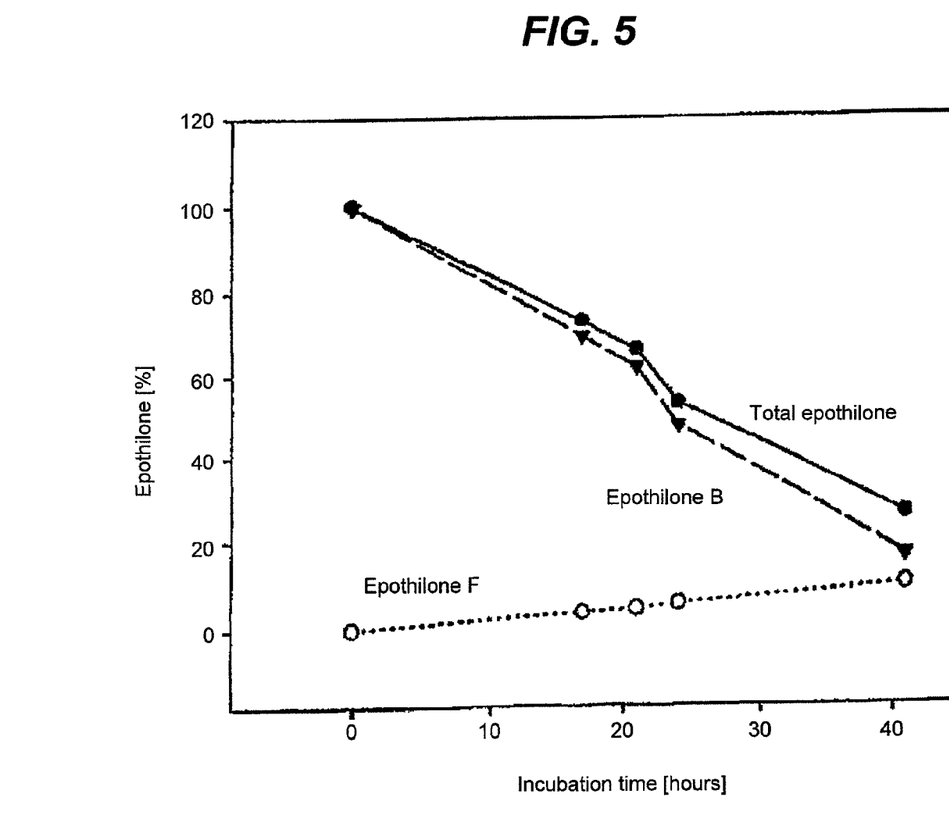
FIG. 5 shows biotransformation of epothilone B to epothilone F.

1) Carrying Out the Biotransformation:

For the biotransformation, a culture of *Sorangium cellulosum* So ce90 is used which has been shaken for four days in the presence of 2% XAD 16 adsorber resin (Rohm and Haas, Frankfurt/M.) at 30° C. and 160 rpm. The culture medium has the following composition in g/litre of distilled water: potato starch (Maizena), 8; glucose (Maizena), 8; defatted soya flour, 2; yeast extract (Marcor), 2; ethylenediaminetetraacetic acid, iron(III) sodium salt, 0.008; $MgSO_4 \times 7H_2O$, 1; $CaCl_2 \times 2 H_2O$, 1; HEPES 11.5. The pH is adjusted to 7.4 before autoclaving with KOH. The XAD is separated from the culture by sieving through a stainless steel sieve (200 µm mesh width). The bacteria are sedimented by centrifugation for 10 min at 10,000 rpm and the pellet is resuspended in ⅕ of the culture supernatant. Epothilone A or epothilone B in methanolic solution is then added to the concentrated bacterial suspension in a concentration of 0.5 g/litre. The culture is cultured further as described above. To analyse the biotransformation, a 1 ml sample is taken at the desired times, 0.1 ml of XAD is added and the sample is shaken at 30° C. for 30 min. The XAD is eluted with methanol. The eluate is concentrated to dryness and taken up again in 0.2 ml of methanol. This sample is analysed by means of HPLC. FIG. 4) Kinetics of the biotransformation of epothilone A to epothilone E FIG. 5) Kinetics of the biotransformation of epothilone B to epothilone F.

2) Preparation of Epothilone E by Biotransformation of 1 g of Epothilone A.

The strain *Sorangium cellulosum* So ce90 is grown for four days in 8.5 l of the above medium (but without XAD addition) in a 10 litre bioreactor at 30° C., a speed of rotation of 150 rpm and an introduction of 1 l/min of air.

The culture is then concentrated to 3 l by crossflow filtration. For this purpose, 0.6 m$^2$ of a membrane having a pore size of 0.3 µm are used.

The concentrated culture is transferred to a 4 litre bioreactor and a methanolic solution of 1 g of epothilone A in 10 ml of methanol is added. The culture is then cultured further for a period of time of 21.5 h. The temperature is 32° C., the stirrer speed is 455 rpm and the introduction of air takes place at 6 l/min. At the time of harvesting, 100 ml of XAD is added and the mixture is incubated further for 1 h. The XAD is separated from the cells by screening and exhaustively eluted with methanol. The concentrated eluate is analysed by means of HPLC.

Balancing of the Biotransformation:

Epothilone A employed: 1000 mg=100%
Epothilone A recovered after 21.5 h: 53.7 mg=5.4%
Epothilone E formed after 21.5 h: 661.4 mg=66.1%
Epothilone A completely decomposed:=28.5%

Example 5

The epothilones according to the invention were tested with cell cultures (Table 2) and for promotion of polymerization (Table 3).

TABLE 2

Epothilone tests with cell cultures

| | Epothilone | | | | | |
|---|---|---|---|---|---|---|
| | A | B | C | D | E | F |
| | 493 | 507 | 477 | 491 | 509 | 523 |
| | | | IC-50 [ng/ml] | | | |
| Mouse fibroblasts L 929 | 4 | 1 | 100 | 20 | 20 | 1.5 |
| human tumor cell lines: | | | | | | |
| HL-60 (leukaemia) | 0.2 | 0.2 | 10 | 3 | 1 | 0.3 |
| K-562 (leukaemia) | 0.3 | 0.3 | 20 | 10 | 2 | 0.5 |
| U-937 (lymphoma) | 0.2 | 0.2 | 10 | 3 | 1 | 0.2 |
| KB-3.1 (carcinoma of the cervix) | 1 | 0.6 | 20 | 12 | 5 | 0.5 |
| KB-VI (carcinoma of the cervix multires) | 0.3 | 0.3 | 15 | 3 | 5 | 0.6 |
| A-498 (carcinoma of the kidney) | — | 1.5 | 150 | 20 | 20 | 3 |
| A-549 (carcinoma of the lung) | 0.7 | 0.1 | 30 | 10 | 3 | 0.1 |

TABLE 3

Polymerization test with epothilones

| Measurement: | w | x | y | z | Agent [s] | Agent [%] |
|---|---|---|---|---|---|---|
| Control | 200 | 170 | 180 | 210 | 190 | 100 |
| Epothilone A | 95 | 60 | 70 | 70 | 74 | 39 |
| Epothilone B | | 23 | 25 | 30 | 26 | 14 |
| Epothilone C | 125 | 76 | 95 | 80 | 94 | 49 |
| Epothilone D | 125 | 73 | 120 | | 106 | 56 |
| Epothilone E | 80 | 60 | 50 | 45 | 59 | 31 |
| Epothilone F | 80 | 40 | 30 | 50 | 50 | 26 |

Parameter: Time up to the half-maximal polymerization of the control

Standard Test with 0.9 mg of Tubulin/ml and 1 μM Sample Concentration

The polymerization test is an in vitro test using purified tubulin from pigs' brain. Evaluation is carried out photometrically. Polymerization-promoting substances such as the epothilones reduce the time up to which half-maximal polymerization has taken place, i.e. the shorter the time, the more active the compound. w, x, y and z are four independent experiments, the relative activity is expressed in the last column in % of the control; again the lowest values indicate the best activity. The ranking list corresponds reasonably accurately to that found in cell cultures.

The invention claimed is:

1. A process of making epothilone E comprising fermenting a strain of *Sorangium cellulosum* in the presence of a resin, wherein the epothilone E produced by the strain of *Sorangium cellulosum* is bound to the resin.

2. The process of claim 1, further comprising separating the epothilone E from the resin.

3. Epothilone E produced by the process of claim 2.

4. A process of making epothilone F comprising fermenting a strain of *Sorangium cellulosum* in the presence of a resin, wherein the epothilone F produced by the strain of *Sorangium cellulosum* is bound to the resin.

5. The process of claim 4, further comprising separating the epothilone F from the resin.

6. Epothilone F produced by the process of claim 5.

7. Epothilone E bound to a resin.

8. Epothilone F bound to a resin.

* * * * *